(12) United States Patent
Roach (10) Patent No.: US 8,942,637 B2
(45) Date of Patent: Jan. 27, 2015

(54) COMFORT DEVICE, SYSTEM AND METHOD WITH ELECTRONIC MESSAGE DISPLAY

(71) Applicant: Sean Roach, Carson City, NV (US)

(72) Inventor: Sean Roach, Carson City, NV (US)

( * ) Notice: Subject to any disclaimer, the term of this patent is extended or adjusted under 35 U.S.C. 154(b) by 0 days.

(21) Appl. No.: 13/830,848

(22) Filed: Mar. 14, 2013

(65) Prior Publication Data

US 2013/0344839 A1 Dec. 26, 2013

Related U.S. Application Data

(60) Provisional application No. 61/663,436, filed on Jun. 22, 2012.

(51) Int. Cl.
*H04B 7/26* (2006.01)
*H04W 84/00* (2009.01)

(52) U.S. Cl.
CPC ........ *H04B 7/26* (2013.01); *H04W 84/00* (2013.01)
USPC .......... 455/66.1; 455/550.1; 455/344; 463/39

(58) Field of Classification Search
CPC ............ H04B 7/00; H04B 7/26; H04B 10/00; H04W 84/00; H04W 84/10; H04W 84/12; A63H 3/00; A63H 3/28; A63H 3/52
See application file for complete search history.

(56) References Cited

U.S. PATENT DOCUMENTS

| | | | |
|---|---|---|---|
| 5,636,994 A | 6/1997 | Tong | |
| 5,733,131 A | 3/1998 | Park | |
| 6,312,307 B1 | 11/2001 | Dean, II | |
| 6,352,478 B1 | 3/2002 | Gabai et al. | |
| 6,742,188 B1 | 5/2004 | Del Castillo | |
| 6,773,344 B1 | 8/2004 | Gabai et al. | |
| 6,800,013 B2 | 10/2004 | Liu | |
| 7,853,645 B2 | 12/2010 | Brown et al. | |
| 2001/0021669 A1 | 9/2001 | Gabai et al. | |
| 2002/0107591 A1* | 8/2002 | Gabai et al. | 700/94 |
| 2003/0027636 A1 | 2/2003 | Covannon et al. | |
| 2004/0049393 A1 | 3/2004 | Duran et al. | |
| 2008/0153594 A1* | 6/2008 | Zheng | 463/39 |
| 2009/0197504 A1* | 8/2009 | Hsu | 446/301 |
| 2010/0093434 A1 | 4/2010 | Rivas | |

(Continued)

FOREIGN PATENT DOCUMENTS

DE 10 2007 045 129 4/2009
GB 2 360 171 9/2001

OTHER PUBLICATIONS

International Search Report and Written Opinion dated Apr. 21, 2014, from related international application No. PCT/US2013/046033.

*Primary Examiner* — Thanh Le
(74) *Attorney, Agent, or Firm* — Foley & Lardner LLP (57) ABSTRACT

A message playing system includes a plurality of comfort devices, each having a soft, huggable body and an electronic circuit in the body. The electronic circuit includes a WiFi or other wireless communication circuit for wireless electronic message communications. Each comfort device includes a display device for displaying messages. A server is connected over a communication network that includes at least one wireless communication link to each comfort device. The server is configured to receive and store messages and identification information for each message. The server is further configured to transmit the plurality of messages from the server to the comfort devices associated with the messages.

19 Claims, 5 Drawing Sheets

(56) References Cited

U.S. PATENT DOCUMENTS

| | | | |
|---|---|---|---|
| 2011/0001892 A1* | 1/2011 | Gay | 348/836 |
| 2011/0009175 A1 | 1/2011 | Raichman et al. | |
| 2011/0028067 A1 | 2/2011 | Forks et al. | |
| 2011/0106283 A1 | 5/2011 | Robinson | |

* cited by examiner

Registration Page

Enter ID No.     [__________] 40

Place of Purchase [__________] 41

Date of Purchase [__________] 42

Name of Owner [__________] 43

FIG. 4

Message Input Page

Enter ID No. [__________] 50

Enter Text Message [__________] 54

Record Message [START] [STOP] } 52

FIG. 5

COMFORT DEVICE, SYSTEM AND METHOD WITH ELECTRONIC MESSAGE DISPLAY

CROSS-REFERENCE TO RELATED PATENT APPLICATIONS

This application claims priority from Provisional Application U.S. Application 61/663,436, filed Jun. 22, 2012, incorporated herein by reference in its entirety.

BACKGROUND

Field of the Disclosure

This disclosure relates to comfort devices that include message display capabilities and communication network connections for receiving message information, and systems and methods that employ such devices and, in particular embodiments, to a stuffed animal or other stuffed, plush or soft item for providing comfort to a user and that includes processing and communication electronics for wireless WiFi communication with a server over a network to receive and store messages for selective display.

SUMMARY

Embodiments of the present invention relate, generally to comfort devices that include wireless communication and message display capabilities, and systems and methods that employ such devices. In particular embodiments, the comfort device comprises a stuffed animal, pillow or other stuffed, plush or soft item that is typically used for providing comfort to a user. According to embodiments of the present invention, the comfort device includes processing and communication electronics for wireless communication with a server over a network, and one or more electronic display devices. The communication electronics are configured to communicate, through a wireless link (such as, but not limited to a WiFi connection to the Internet or other wide area network), with the server to receive and store messages for selective display on the electronic display device.

A message playing system according to an embodiment of the invention includes a comfort device that has a soft body and is configured to be held or hugged to provide comfort to a device user. The system according to that embodiment also includes an electronic circuit disposed within the body of the comfort device. The electronic circuit has a wireless communication circuit for receiving wireless electronic message communications. In addition, the system according to that embodiment also includes a display device connected to the electronic circuit for displaying one or more messages associated with wireless electronic message communications received by the wireless communication circuit.

In a message playing system according to a further embodiment of the invention the wireless communication circuit comprises a WiFi communication circuit that communicates electronic messages through a direct wireless link to a wireless communication network.

In a message playing system according to a further embodiment of the invention, the wireless communication circuit comprises a WiFi communication circuit that communicates electronic messages through a wireless link to a communication network, the wireless link including a network communication device connected via a wired connection to the communication network, the network communication device being connected for wireless communication with the wireless communication circuit in the comfort device.

In a message playing system according to a further embodiment of the invention, the wireless communication circuit comprises a WiFi communication circuit that continuously or periodically monitors a wireless communication link for a wireless communication message.

In a message playing system according to a further embodiment of the invention, the wireless communication circuit comprises at least one of a radio frequency (RF) or a Bluetooth communication circuit that communicates electronic messages through a direct wireless link to a wireless communication network.

In a message playing system according to a further embodiment of the invention, a server is connected for communication with the comfort device, over a communication network, including at least one wireless communication link, where the server is configured to: receive over the communication network and store at least one message and identification information associated with the message, the identification information identifying the comfort device as being associated with the message; and transmit the at least one message from the server to the comfort device associated with the message.

In a message playing system according to a further embodiment of the invention, the server is configured to transmit the at least one message to the comfort device in response to at least one of an expiration of a predetermined time period, a predefined time being reached, and a request being received from a user of the comfort device.

In a message playing system according to a further embodiment of the invention, an electronic memory is disposed in the comfort device, for storing at least one message received from the server. In addition, the server includes a further electronic memory for storing a plurality of messages and identification information associated with each message. In such embodiments, the electronic memory disposed in the comfort device stores at least one message received from the server while the server stores at least one additional message and identification information that associates the at least one additional message with the comfort device.

In further example of a message playing system according to the above-described embodiment of the invention, the server is configured to transmit the at least one additional message to the comfort device in response to at least one of an expiration of a predetermined time period, a predefined time being reached, and a request being received from a user of the comfort device.

In a message playing system according to a further embodiment of the invention, a pressure activated electrical switch is disposed in or on the comfort device and arranged to be activated upon the soft body of the comfort device being hugged.

A message playing system according to a further embodiment of the invention includes a housing that contains the electronic circuit. In such embodiments, the housing is sealed to inhibit leakage of fluid from outside of the housing to the electronic circuit contained within the housing. In addition, a volume of stuffing is provided around the housing.

In a message playing system according to a further embodiment of the invention, the comfort device comprises a stuffed animal.

A message playing system according to a further embodiment of the invention includes a further display device connected to the electronic circuit and controlled by the electronic circuit to display an indication that a message is available to be played. In such embodiments, the further display device that displays an indication that a message is available to be played is separate from the display device that displays the one or more messages received.

A message playing system according to a further embodiment of the invention includes a server connected for communication with the comfort device, over a communication network, including at least one wireless communication link. In such embodiments, the server provides a network site at which one or more network users are able to enter message information and designate a comfort device to associate with the message information. Also in such embodiments, the server is configured to communicate message information to the comfort device designated as being associated with the message information.

A message playing system according to a further embodiment of the invention includes a plurality of comfort devices, where each comfort device has a soft body and is configured to be held or hugged to provide comfort to a device user. Each comfort device includes an electronic circuit disposed within the body of the comfort device, where the electronic circuit includes a wireless communication circuit for receiving wireless electronic message communications. Each comfort device includes a display device connected to the electronic circuit for displaying one or more messages associated with wireless electronic message communications received by the wireless communication circuit. The system further includes a server connected for communication with the plurality of comfort devices, over a communication network, including at least one wireless communication link to each comfort device. The server is configured to receive over the communication network and store a plurality of messages and identification information for each message. The identification information for each message identifies at least one of the comfort devices as being associated with the message. The server is further configured to transmit the plurality of messages from the server to the comfort devices associated with the messages.

A message playing method according to a further embodiment of the invention includes disposing an electronic circuit within the body of the comfort device, where the electronic circuit includes a wireless communication circuit for receiving wireless electronic message communications. The method further includes connecting a display device to the electronic circuit for displaying one or more messages associated with wireless electronic message communications received by the wireless communication circuit.

In a method according to a further embodiment, the wireless communication circuit comprises a WiFi communication circuit, and the method further comprises receiving wireless electronic message communications through a direct WiFi link of the wireless communication circuit in the comfort device to a wireless communication network.

In a method according to further embodiments, the wireless communication circuit comprises a WiFi communication circuit, and the method further comprises receiving wireless electronic message communications through a wireless link to a communication network. In such embodiments, the wireless link includes a network communication device connected via a wired connection to the communication network, where the network communication device is connected for WiFi communication with the wireless communication circuit in the comfort device.

In a method according to a further embodiment, the wireless communication circuit comprises a WiFi communication circuit, the method further comprising continuously or periodically monitoring, via the WiFi communications circuit, a wireless communication link for a wireless communication message.

A method according to further embodiments includes connecting a server for communication with the comfort device, over a communication network, including at least one wireless communication link. Such embodiments further include configuring the server to receive over the communication network and store at least one message and identification information associated with the message, the identification information identifying the comfort device as being associated with the message; and configuring the server to transmit the at least one message from the server to the comfort device associated with the message.

DETAILED DESCRIPTION

The detailed description set forth below in connection with the appended drawings is intended as a description of various aspects of the present disclosure and is not intended to represent the only aspects in which the present disclosure may be practiced. Each aspect described in this disclosure is provided merely as an example or illustration of the present disclosure, and should not necessarily be construed as preferred or advantageous over other aspects. The detailed description includes specific details for providing a thorough understanding of the present disclosure. However, it will be apparent to those skilled in the art that the present disclosure may be practiced without these specific details. In some instances, well-known structures and devices are shown in block diagram form in order to avoid obscuring the concepts of the present disclosure. Acronyms and other descriptive terminology may be used merely for convenience and clarity and are not intended to limit the scope of the present disclosure.

While for purposes of simplicity of explanation, the methodologies are shown and described as a series of acts, it is to be understood and appreciated that the methodologies are not limited by the order of acts, as some acts may, in accordance with one or more aspects, occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with one or more aspects.

Embodiments of the present invention relate, generally to comfort devices that include wireless communication and message display capabilities, and systems and methods that employ such devices. In particular embodiments, the comfort device comprises a stuffed animal, pillow or other stuffed, plush or soft item that is typically used for providing comfort to a user. According to embodiments of the present invention, the comfort device includes processing and communication electronics for wireless communication with a server over a network, and one or more electronic display devices. The communication electronics are configured to communicate, through a wireless link (such as, but not limited to a WiFi connection to the Internet or other wide area network), with the server to receive and store messages for selective display on the electronic display device.

The server provides a user interface, such as, but not limited to, one or more websites with pages that allow device users to register comfort devices and access additional stored messages, and other network users to submit messages to play on registered comfort devices. In particular embodiments, the messages are in the form of electronic audio messages, such as, but not limited to, recorded voice messages, musical messages, or other audible information. In other embodiments, the messages may alternatively or additionally include electronic video messages, electronic text messages, combinations thereof, and/or other electronic information. The user interface allows the network users to identify one or more particular comfort devices to associate with the submitted message. Once a message has been submitted to the server, the server provides the submitted message to the one or more comfort devices that are associated with the submitted message. In particular embodiments, the server may send a predefined number of messages to a comfort device (where the predefined number may be one or any suitable number greater than one, for example, but not limited to five). However, the server may store additional messages that can be sent to the comfort device at a later time and/or that can be accessed by a device user, for example, through a device user website page provided by the server.

The comfort devices may be used in the manner that an ordinary comfort device (such as, but not limited to, a stuffed animal, pillow or the like) is used. However, when the comfort device of embodiments of the present invention is in an appropriate range of a wireless signal provider, electronics associated with the comfort device receive communication signals that include one or more messages that can be played (displayed) on a display device associated with the comfort device.

Messages are received by the comfort devices, through wireless communication links. Once a message is received (or available to be received), a first display device on or associated with the comfort device is activated to inform a device user that a message is available. The device user may activate a user-operable switch to activate display electronics in the comfort device to display the message on a second display device (or on the first display device).

Figure 1:
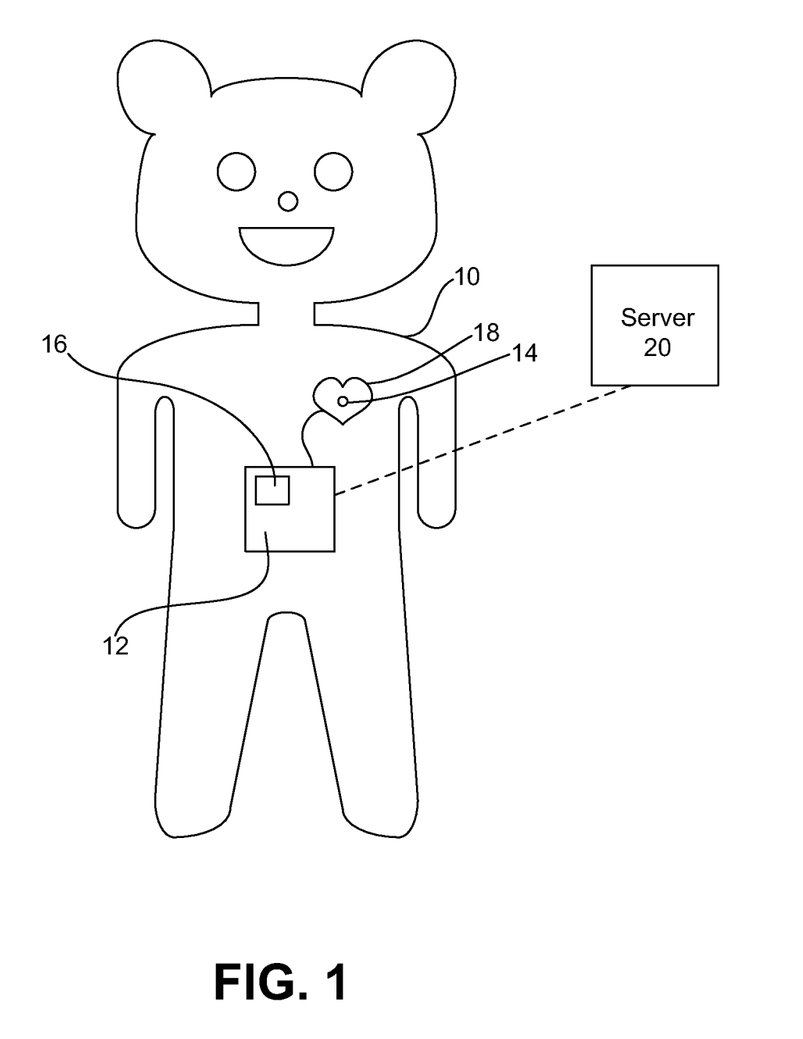
FIG. 1 is general representation of an example of a comfort device in the form of a stuffed bear animal and server according to an embodiment of the present invention.

An example of a comfort item 10, in the form of a stuffed bear, is shown in FIG. 1. A stuffed bear is used in examples illustrated and described herein, as an expedient to describing various aspects of the invention. However, further embodiments of the invention employ other types of comfort items, such as those described below.

The comfort item 10 includes an electronic circuit 12. In the embodiment of FIG. 1, the electronic circuit 12 is located inside of the body of the stuffed bear comfort item 10, hidden from view from outside of the body of the bear. A sufficient amount of stuffing and/or other soft material is placed around the electronic circuit 12, to protect the electronic circuit 12 and/or to obscure its presence in the body of the stuffed bear comfort item 10. In other embodiments, the electronic circuit 12 may be attached on an outer surface of the comfort item 10.

The comfort item 10 may include one or more visible features that enhance the comfort or endearing qualities of the item, including, but not limited to facial features (such as eyes, nose, mouth), ears, arms, legs, a heart-shaped feature, and the like. In particular embodiments of the invention, a first electronic display device 14 is incorporated in (or associated in another manner with) one or more of such visible features. In particular embodiments, the first electronic display device 14 comprises one or more electronic light emitting devices that emit a light when activated. In other embodiments, the first electronic display device alternatively or additionally includes one or more of a sound emitting device, video or text display screen device, or a tactile output device, that is electrically connected to the electronics 12 and controlled by the electronics 12 to selectively activate to provide a first display comprising an audible, visual, and/or tactile indication that a message is available.

Once a message is available, a second electronic display device 16 is selectively activated by the electronics 12 to provide a second display, comprising the message. In particular embodiments, the second electronic display device 16 comprises an audio display device (such as, but not limited to, a speaker and audio signal generator), for playing audio messages, such as, but not limited to voice messages, musical messages or other audible information. In other embodiments, the second electronic display device alternatively or additionally comprises a visual display device (such as, but not limited to an electronic display screen and an image or video signal generator) or a combination thereof, that can display one or more of still image information, moving or video information, textual information, or various combinations thereof, and is located in an externally visible location on the comfort device 10. In further embodiments, the first and second displays are provided by a single electronic display device (obviating the need for two display devices).

In the embodiment of FIG. 1, the first display device 14 comprises a light emitting device, such as, but not limited to one or more LED, incandescent, fluorescent or other lamp. The first display device 14 in FIG. 1 is included in a heart-shaped feature 18 on the chest area of the body of the stuffed bear. In other embodiments, the light emitting display device 14 (or a further light emitting device 14) may be included in one or both of the eye features, one or both of the ear features, the nose feature, the mouth feature or other locations on the stuffed bear comfort item 10.

In the embodiment of FIG. 1, the second display device 16 comprises a speaker and audio signal generator, and is incorporated in the electronics 12 so as to be hidden from view. In other embodiments, the second display device 16 may be located in a separate location on the comfort device 10 relative to the location of the electronics 12, but electrically connected to the electronic circuit 12 through suitable electronic conductors.

The electronic circuit 12 provides various functions described herein, including communications through a communications link with a network server 20 to receive messages, storing received messages, and selectively playing stored messages. The communications link includes a wireless link 22 that directly connects the electronic circuit 12 to the server 20, or to further communications electronics that are connected (through other wired and/or wireless links) to the server 20.

Figure 2A:
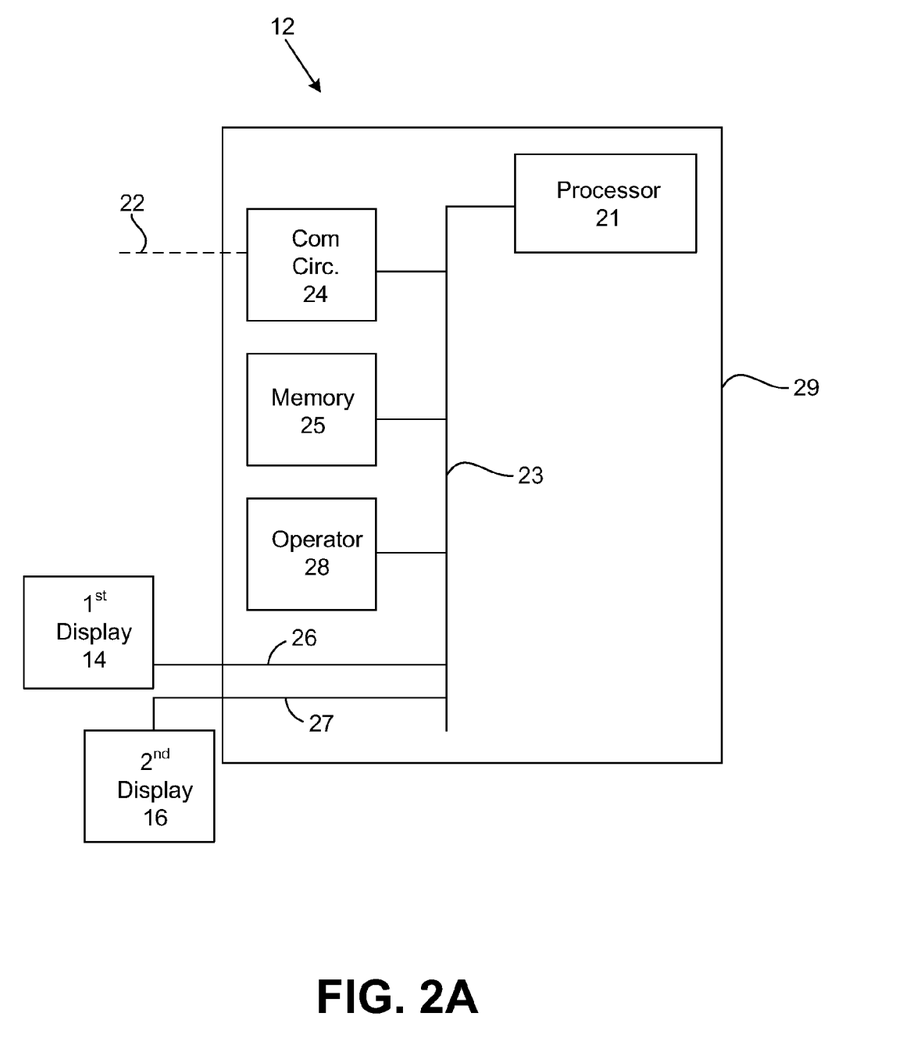
FIG. 2A is a block diagram representation of an electronic circuit included in a comfort device, in accordance with an embodiment of the present invention.
Figure 2B:
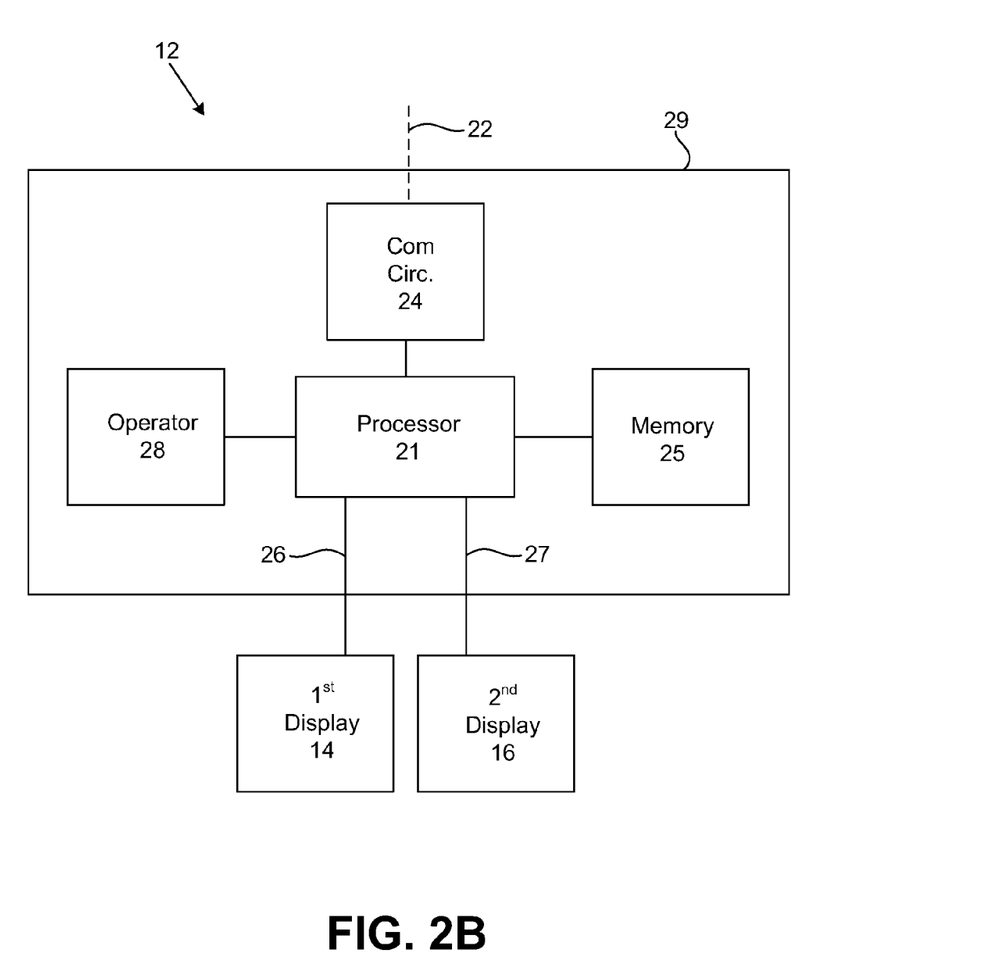
FIG. 2B is a block diagram representation of an electronic circuit included in a comfort device, in accordance with another embodiment of the present invention.

FIG. 2*a* shows a generalized block diagram of an example embodiment of the electronic circuit 12, connected to the first and second display devices 14 and 16. FIG. 2*b* shows a generalized block diagram of another example embodiment of the electronic circuit 12, connected to the first and second display devices 14 and 16. The embodiment of FIG. 2a employs a bus-type architecture, in which a processor 21 and various components of the electronic circuit are connected to a common bus 23. In contrast, in the embodiment of FIG. 2b, various components of the electronic circuit are connected, individually, to the processor 21, through individual electronic connections. Other embodiments may employ a combination or hybrid of a bus type architecture and individual connections. Yet other embodiments may employ other suitable connection arrangements for components of the electronic circuit 12.

In each of the electronic circuit 12 embodiments of FIGS. 2a and 2b, the processor 21 comprises one or more processing devices configured with hardware, firmware, or combinations thereof and/or programmed with software to provide functions as described herein. The electronic circuit 12 also includes a communication circuit 24, electronic memory 25, an electrical connection 26 to the first display device 14, an electrical connection 27 to the second display device 16 and an operator 28. The electronic circuit 12 includes other components (not shown), including a power source (or a connection to a power source) for providing electrical power to the components of the electronic circuit 12. In addition, the electronic circuit 12 may include an outer casing 29 configured to cover and protect the electronic components of the electronic circuit 12, including, for example, to keep stuffing or other material located inside of the comfort device 10 from coming into contact with sensitive electronics. In particular embodiments, the casing 29 is sufficiently sealed to prevent moisture from coming into contact with the electronic circuit 12. In yet further embodiments, the casing 29 is sufficiently sealed against water leakage to allow the comfort device 10 to be washed (for example in a clothes washing machine), without damaging the electronic circuit 12.

The communications circuit 24 includes suitable electronics for providing and supporting wireless communication with the communications device 32 ($32^1$, $32^2$ ... $32^n$). The communications circuit 24 may include receiver or transceiver electronics that support one or more types of wireless communication protocols, as described below.

The electronic memory 25 comprises one or more electronic memory circuits capable of storing one or more messages received, over the network 30, from the server 20. In particular embodiments, the electronic memory 25 is configured to store multiple messages that can be selectively and individually retrieved for display on the second display device 16, under control of the processor 21. For example, the electronic memory 25, under control of the processor 21, may be configured to store a predefined number of messages (where the predefined number may be any suitable number, including one or a number greater than one). In one example embodiment, the predefined number is five, such that the electronic memory 25 stores up to five messages at any one time. As described below, one or more of such messages may be received from the server 20 or may be pre-stored in the memory 25 at a time of manufacture of the comfort device or other time before the comfort device is sold or otherwise provided to a device user.

Each of the electrical connections 26 and 27 comprises one or more suitable electrical conductive paths, cables, wires, terminals or connectors that connect the electronics 12 to communicate electronic display signals for electronic display of information on the display devices 14 and 16. They type of electrical connection 26 and 27 employed in a particular embodiment can depend upon the type of display devices used for the first and second display devices 14 and 16.

The operator 28 comprises any suitable electronic switch device that is operated by manual or other designated action. In one embodiment the operator 28 comprises a pressure-activated switch that changes state or activates (e.g., closes or turns ON) when a squeezing pressure is applied to the comfort device 10 (or to a designated location on the comfort device 10, such as, but not limited to the chest area of the body, a paw, an ear, the nose or the like). Thus, for example, a pressure-activated switch may be arranged in the body area of the comfort device 10, to activate (e.g., close or turn ON) when a device user hugs or otherwise squeezes the comfort device 10 with sufficient force to change the state of the pressure-activated switch.

Alternatively, or in addition, the operator 28 comprises a pressure-activated switch arranged in a paw, ear, nose or other area of the comfort device 10, to activate when a device user manually squeezes that area of the comfort device 10. In other embodiments, the operator 28 may comprise other suitable manually operable switch devices including, but not limited to, a standard push-button switch, toggle switch, knob, touch pad or the like, arranged at a suitable location on the comfort device 10 for selective activation by a device user. Alternatively or in addition, the operator 28 comprises a switch configured to activate (e.g., close or turn ON) upon detection of the occurrence of a specified event, such as, but not limited to the reaching of a predetermined time or date, the passage of a predetermined time period, the detection of motion in the proximity of the comfort device 10 (e.g., within a specified distance from the comfort device 10), the detection of light, a change in light intensity or absence of light, the detection of motion, or the detection of another activity or event. Accordingly, the operator 28 may comprise a proximity detector, a light detector, a motion detector, a clock or other timer device, or other suitable device that electrically indicates the occurrence of a specified activity or event.

As described in more detail, below, the operator 28 may be activated by a device user, when the device user desires to hear or view a stored message. Alternatively, or in addition, the operator 28 may be activated automatically, for example, in response to the detection of an occurrence of a specified activity or event, such as described above. When the operator 28 is activated, the electronic circuit 12 (under the control of the processor 21) retrieves one or more pre-stored messages from the memory 25 and displays the message through the second display device 16. In further embodiments, a first activation of the operator 28 causes the electronic circuit 12 to retrieve one of multiple pre-stored messages from the memory 25 and displays that message through the second display device 16, while a second activation of the operator 28 (e.g., any time after the first activation, or in further embodiments within a predefined time after the first activation of the operator 28) causes the electronic circuit 12 to retrieve and display a second stored message from the memory 25. Similar operations can cause playing of a third and further messages stored in memory 25. In yet further embodiments, one or more (or all) of the message are not pre-stored in the memory 25 and, instead, the electronic circuit 12 retrieves a message from the server 20 in response to the operator 28 being activated as described above.

In particular embodiments, the first display device 14 may be activated by the electronic circuit 12 to inform a device user of a stored message (or a new message). In such embodiments, when the device user sees, hears or feels the first display device 14 being activated, the device user may be informed that a message is available to hear or view. The operator 28 may be activated by a device user, when the device user desires to play (hear or view) a stored message. In particular embodiments, the device user may activate the operator 28 to play a stored message at any time, whether or not the first display 14 is activated. In other embodiments, the electronic circuit 12 controls access to stored messages to allow a device user to play a stored message only if and when the first display 14 is also being activated. In yet other embodiments that do not include a first display device 14, the device user need not be informed of a new or stored message, but may still play a stored message or messages by activation of the operator 28. When the operator 28 is activated by the device user, the electronic circuit 12 (under the control of the processor 21) retrieves a message from the memory 25 and displays the message through the second display device 16. In further embodiments, the electronic circuit 12 retrieves a message from the server 20 in response to the operator 28 being activated.

A system employing a plurality of comfort devices 10 (labeled $10^1, 10^2 \ldots 10^n$, where n represents any number greater than 2), each coupled for communication over a network 30 with the server 20 is described with reference to FIG. 3. The comfort devices $10^1, 10^2 \ldots 10^n$ may be located in mutually different geographic areas, for example, in different countries, cities, neighborhoods and/or buildings. Alternatively, some or all of the comfort devices $10^1, 10^2 \ldots 10^n$ may be located in proximity of each other, for example, in the same room, building or campus.

Figure 3:
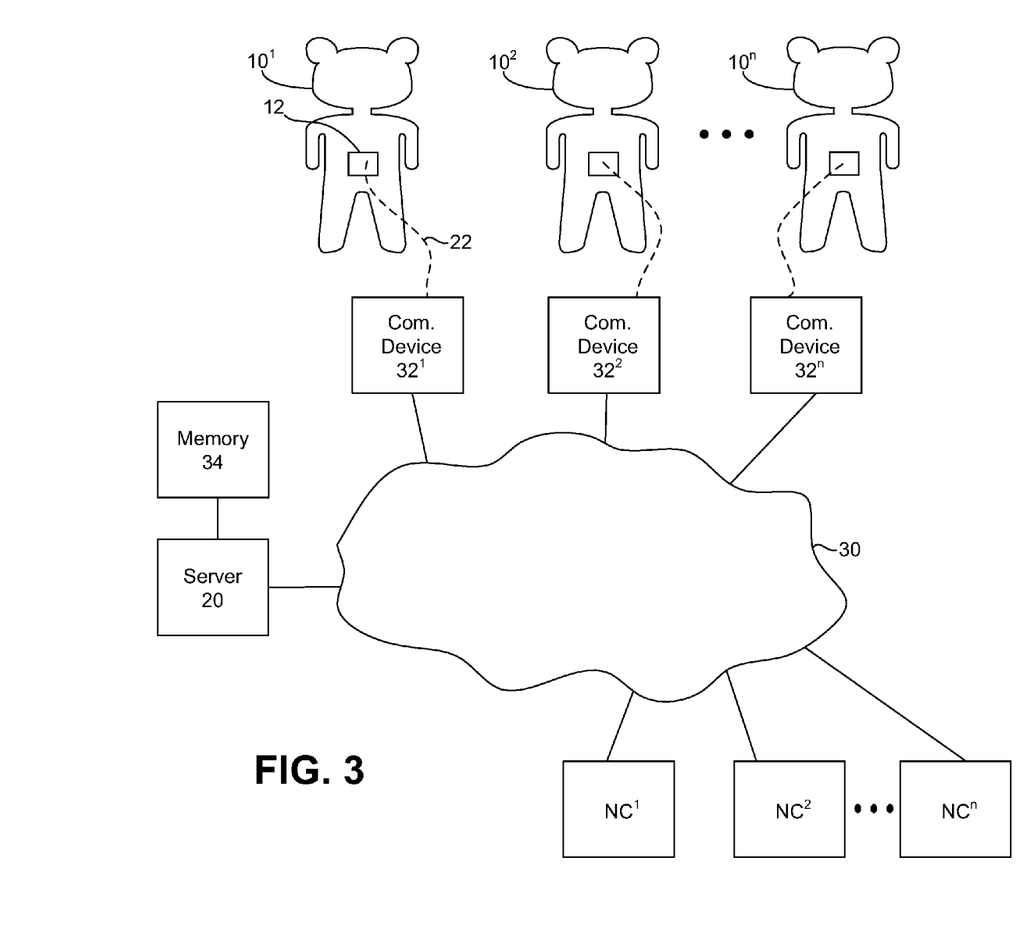
FIG. 3 is a block diagram representation of a network system employing comfort devices according to an embodiment of the present invention.

Each comfort device $10^1, 10^2 \ldots 10^n$ in FIG. 3 corresponds to a different respective comfort device configured as described above with reference to comfort device 10. In the embodiment of FIG. 3, the electronic circuit (corresponding to circuit 12 in FIGS. 1, 2a and 2b) of each respective comfort device $10^1, 10^2 \ldots 10^n$ is connected, through a respective wireless link 22, to a respective wired communications device, labeled $32^1, 32^2 \ldots 32^n$ (such as, but not limited to, a local network computer, router, or the like) that is connected through a standard wired connection to the network 30. In other embodiments, any one or more of the communications device $32^1, 32^2 \ldots 32^n$ may be connected to the network 30 through a further wireless link or a combination of wired and wireless links.

The wireless link 22 allows the comfort device ($10^1, 10^2 \ldots 10^n$) to be freely moveable and readily used for typical comfort device activities noted above, without obstructions of wired connections to external devices, while allowing the electronic communications functions described herein to be performed. The wireless link 22 may comprise any suitable communication link that employs wireless communications electronics and protocols, such as, but not limited to, WiFi, radio frequency rf, Bluetooth, optical, magnetic, other electromagnetic links, or the like. The electronic circuit 12 (including the communication circuit 24) and the communications device $32^1, 32^2 \ldots 32^n$ include suitable electronics for supporting communications over one or more of such wireless links.

The server 20 in FIG. 3 (and FIG. 1) comprises one or more computers coupled for communication on the network and that are programmed and/or configured to provide server operations and functions described herein. The server 20 includes or is associated with electronic memory 34 suitable for storing messages received from network user computer $NC^1, NC^2 \ldots NC^n$ (described below) and/or other messages that are pre-stored and/or retrieved by the server 20 from other network locations over the network 30. In some examples, the server 20 comprises a desktop computer, laptop computer, mainframe computer or other computer or set of computers capable of handling the server functions described herein.

FIG. 3 shows a plurality of network user computers (labeled $NC^1, NC^2 \ldots NC^n$) connected for communication with the server 20, over the network 30. The network user computers $NC^1, NC^2 \ldots NC^n$ are operated by network users to input messages, through the server 20, for display on the comfort devices $10^1, 10^2 \ldots 10^n$. Each network user computer $NC^1, NC^2 \ldots NC^n$ comprises a suitable computer device having at least one display device and at least one user input device, to allow a network user to receive information over the network 30 (such as audio, video, text and other information from server 20) and to input information to communicate over the network 30 (such as audio, video, text and other information to the server 20). In some examples, each network user computer $NC^1, NC^2 \ldots NC^n$ comprises a desktop computer, laptop computer, mobile phone or pad computer.

The network user computers $NC^1, NC^2 \ldots NC^n$ may be located in mutually different geographic areas, for example, in different countries, cities, neighborhoods and/or buildings. Alternatively, some or all of the network user computers $NC^1, NC^2 \ldots NC^n$ may be located in proximity of each other, for example, in the same room, building or campus.

According to embodiments of the present invention, device users (or others) who have obtained one or more of the comfort devices $10^1, 10^2 \ldots 10^n$ are able to register their comfort device(s). The comfort device(s) may be registered by any suitable process that allows the server 20 to designate messages to particular comfort devices. In one example, a device user may register a comfort device 10 by submitting registration information to an entity associated with the server 20 (or an entity associated with a website running on the server 20). Such registration information may be submitted by postal mail, electronic mail, telephone, fax or other suitable communication. In another example, the electronic circuit in the comfort device 10 (using the communication circuit 24 under the control of the processor 21) contacts the server 20, through the wireless link 22 and network 30, to automatically submit registration information.

Figure 4:
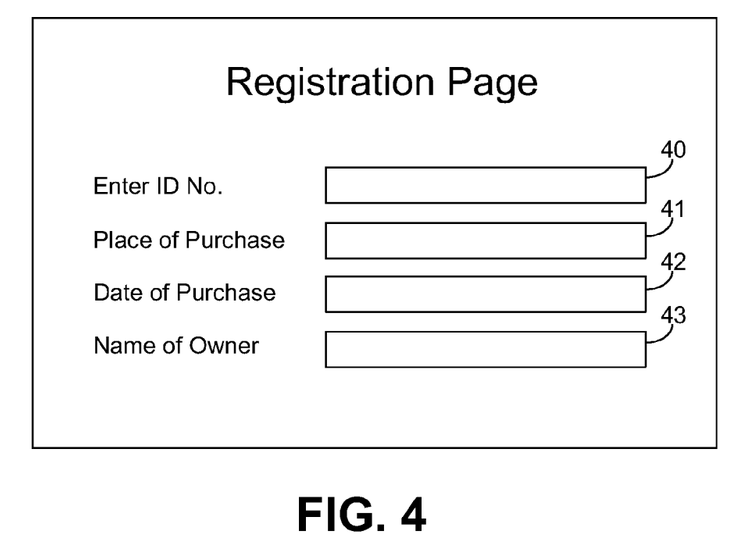
FIG. 4 is a general representation of a network website page for registration of a comfort device, according to an example embodiment of the present invention.

In yet another example, the server 20 provides one or more websites (or other network location) that can be accessed, through the network 30, by a device user (through a suitable network-connected computer, not shown) to register a comfort device 10. In such embodiments, a website provides a page or fields in which the device user can enter registration information and the like. An example of a website page for entering registration information is shown in FIG. 4, where the website page includes a field 40 for entering an identification code (such as, but not limited to, a unique serial number or code, or the like) that is associated with the device user's comfort device 10. The identification code may be printed on the comfort device 10 or included with printed documents, packaging or other materials that are provided with the comfort device 10 when the comfort device 10 is purchased. Alternatively, the identification code may be assigned to a comfort device, at or after the point of purchase. The registration website page (shown in FIG. 4) may include other fields 41-43, for entering other information, such as, but not limited to a place of purchase, a date of purchase, name or other identification of the purchaser or owner of the comfort device, etc.

In certain embodiments, each comfort device $10^1, 10^2 \ldots 10^n$ has a unique identification code that differs from the identification code of each of the other comfort devices $10^1, 10^2 \ldots 10^n$. In other embodiments, a group of multiple (two or more), but not all comfort devices $10^1, 10^2 \ldots 10^n$ includes the same identification code, such that those comfort devices are able to receive the same messages. In yet other embodiments, a comfort device 10 may be associated with more than one identification code, such that messages designated for any one of those identification codes would be accessible by that comfort device.

Once a comfort device is registered, a network user on one of the network user computers $NC^1$, $NC^2$ ... $NC^n$ is able to submit and designate messages for that comfort device. For example, the network user on one of the network user computers $NC^1$, $NC^2$ ... $NC^n$ connects with the server 20, over the communication network 30. In one example, the connection may be accomplished by the network user accessing a website provided by the server 20. Once connected to the server 20, the network user is able to input one or more messages, such as a private or personal message, and designate the message(s) to be played by one or more of the comfort devices $10^1$, $10^2$ ... $10^n$.

Figure 5:
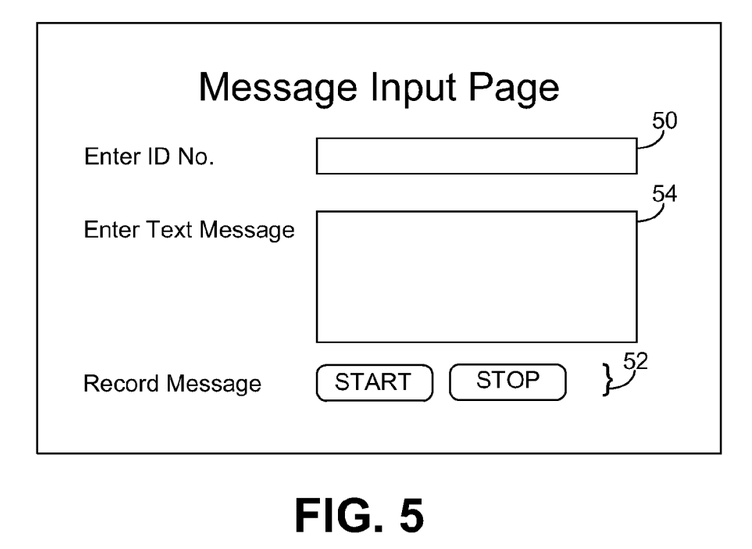
FIG. 5 is a general representation of a network website page for sending a message to a comfort device, according to an example embodiment of the present invention.

Thus, in one embodiment, the server 20 provides a website (or other network location) that can be accessed, through the network 30, by a network user on one of the network user computers $NC^1$, $NC^2$ ... $NC^n$. In such embodiments, the website provides one or more pages or fields in which the network user can enter information, messages and the like. An example of a website page for entering a message is shown in FIG. 5. In the example of FIG. 5, the message input website page includes a field 50 for entering one or more identification numbers associated with one or more of the comfort devices $10^1$, $10^2$ ... $10^n$, to identify the comfort device(s) to which the message is to be sent.

A further field and/or user-operable controls (such as, but not limited to one or more selectable icons or other tabs that a network user can select with a mouse, touchscreen or other computer-input device) is provided on the message input page (or related page), to assist a network user to input one or more messages. For example, in FIG. 5, the message input page includes a set of user-selectable icons 52 (labeled START and STOP) that allow a user to select a starting time (by activating the START icon) and a stopping time (by activating the STOP icon) for entering an audio message. In particular, a network user may activate the START icon to start recording an audio message (such as, but not limited to a voice message) through an audio input device (such as, but not limited to a microphone) associated with the network user's computer $NC^1$, $NC^2$ ..., or $NC^n$. When the network user completes the audio message, the network user may activate the STOP icon. The network user's computer $NC^1$, $NC^2$ ..., or $NC^n$, is controlled to receive and communicate to the server 20, the audio message recorded between activations of the START and STOP icon. Alternatively, the STOP icon may be omitted in embodiments in which a pre-defined recording time is started upon activation of a single icon (such as the START icon), where recording automatically stops after the passage of the pre-defined recording time from the time at which the single icon (e.g., START icon) is activated.

In embodiments in which the comfort device 10 includes a video or image message display device as the second display device 16, the icon(s) 52, or similar icons, are provided to assist the network user in inputting video or image information for the message, for example, through a camera, scanner or other video or image input device associated with the network user's computer $NC^1$, $NC^2$ ..., or $NC^n$, in a manner similar to the manner described above for inputting audio information through a microphone.

In yet further embodiments in which the comfort device 10 includes a visual display screen device that is able to display textual messages, the message input page includes one or more further fields 54 for allowing the network user to input one or more textual messages. The network user may employ the message input website provided by the server 20, to input message information (including one or more messages) and identification information to designate one or more comfort devices $10^1$, $10^2$ ... $10^n$ to receive the message information.

In further embodiments, the server 20 provides one or more further website pages or locations that allow a device user of a registered comfort device $10^1$, $10^2$ ..., or $10^n$ (by using a network-connected computer associated with the device user) to connect with the server and access and view information about messages recorded for that registered comfort device. In one example, such further website pages or locations include selectable icons or fields that allow the device user to select, play and/or delete or revise one or more previously-recorded messages that have been designated for that device user's particular comfort device $10^1$, $10^2$ ..., or $10^n$. For example, a device user may select one or more previously-recorded messages to always be available on that device user's comfort device $10^1$, $10^2$ ..., or $10^n$.

In a further example, such further website pages or locations include selectable icons or fields that allow the device user to select additional messages that have been recorded and designated for that device user's comfort device $10^1$, $10^2$ ..., or $10^n$, but that have not been transmitted from the server 20 to that comfort device. Thus, for example, in embodiments in which the server 20 communicates up to a maximum number (for example, but not limited to, five) recorded messages to a comfort device $10^1$, $10^2$ ..., or $10^n$, the server 20 may store more than the maximum number of messages for that comfort device, and a user of that comfort device may access the further website pages or locations to check for and retrieve any additional messages beyond those that had already been communicated to the comfort device by the server 20 (or older messages that the comfort device had since recorded a new message there-over). In such embodiments, the server 20 is controlled to send additional messages to the designated comfort device, and the designated comfort device is controlled by electronics 12 to store in memory 25, the additional messages for display. In a further example, such further website pages or locations include selectable icons and fields that allow the device user to enter additional information to select an order in which a plurality of messages are to be sent to and/or played by the designated comfort device(s).

Similarly, in further embodiments, the server 20 provides one or more further website pages or locations that allow a network user on a network user's computer $NC^1$, $NC^2$ ..., or $NC^n$ to access and view information about messages that the network user recorded. In one example, such further website pages or locations include selectable icons or fields that allow the network user to select, play and/or delete or revise one or more previously-recorded messages (e.g., to check or improve the recording). In a further example, such further website pages or locations include selectable icons or fields that allow the network user to enter additional information to select an order in which a plurality of messages are to be sent to and/or played by the designated comfort device(s). In such embodiments, the server 20 and/or the electronics 12 receive the additional information input by the network user and controls the sequence or order in which messages are delivered and/or played, based on such additional information.

In a further example, such further website pages or locations include selectable icons or fields that allow the network user to select prerecorded messages (for example, but not limited to, messages that have been recorded by the entity managing or running the server 20 or service associated with the server 20, messages that are available on one or more network sites on the network 30, or the like). Such pre-recorded messages may include, for example, messages recorded by a famous celebrity, sports figure, actor, politician, animated character, or impersonator thereof, that are available to be selected and designated for one or more particular comfort devices $10^1, 10^2 \ldots 10^n$. Thus, for example, a comfort device $10^1, 10^2 \ldots 10^n$ may be in the form of a stuffed animal that has (or is wearing clothes that have) a logo or name of a particular athlete or sports team, and a pre-recorded message that was recorded by that athlete or an athlete on tat team may be selected and designated for that comfort device.

The server 20 stores the messages and associated comfort device designations in the memory 34. Either at the time of receiving the message(s) or at a later time, the server 20 communicates the message(s) to the comfort device(s) designated by the associated designation(s). In particular embodiments, the server 20 communicates with the comfort device(s) over the network 30 and through the wireless link 22.

In one example of such embodiments, the electronic circuit 12 associated with each comfort device $10^1, 10^2 \ldots 10^n$ is configured to maintain a wireless connection that is able to receive network communications of messages from the server 20 at any given time that a message becomes available. In other embodiments, the electronic circuit 12 is configured to periodically (for example, at designated times or after designated time intervals) communicate with the server to check for and retrieve messages. In yet other embodiments, the electronic circuit 12 is configured to communicate with the server to check for and retrieve messages in response to the activation by the user of a manual operator, such as the operator 28 described above.

In particular embodiments, when a message is retrieved by the electronic circuit 12, the electronic circuit 12 activates the first display device 14. For example, with reference to FIGS. 2a and 2b, the processor 21 is configured to control the communication circuit 24 to receive a message from the server 20 and control the activation of the first display device 14, through the connection 26.

In further embodiments, before the server 20 sends a message to a comfort device $10^1, 10^2 \ldots 10^n$, the server 20 first communicates an alert message to the comfort device $10^1, 10^2 \ldots 10^n$ to indicate that a message designated for that comfort device has been received by the server 20. In response to the alert message, the electronic circuit 12 of the designated comfort device $10^1, 10^2 \ldots 10^n$ activates the first display device 14, to alert the device user of the message.

The device user may then operate the operator 28 to retrieve and play the message. In response to operation of the operator 28, the electronic circuit 12 (through the communication electronics 24, wireless link 22 and network 30) communicates with the server 20 to retrieve the message. Upon retrieving the message, the electronic circuit 12 causes the message to be played through the second display device 16.

Thus, according to an example embodiment, a network user on one of the network user computers $NC^1, NC^2 \ldots NC^n$ is able to connect (in a network communications session) with the server 20, to submit information designating a particular comfort device 10 ($10^1, 10^2 \ldots 10^n$) and submit a message for the designated comfort device. In one embodiment, the message is one or more audio messages that the network user enters, using an audio input device (such as, but not limited to, a microphone) associated with the network user's computer $NC^1, NC^2 \ldots NC^n$. In another embodiment, the message is one or more still images that the network user enters, using an image input device (such as, but not limited to, a scanner, a still image camera, or the like) associated with the network user's computer $NC^1, NC^2 \ldots NC^n$. In yet another embodiment, the message is one or more moving image or videos that the network user enters, using a video input device (such as, but not limited to a video camera, or the like). In yet other embodiments, the message is one or more textual messages that the network user enters, using a text input device (such as, but not limited to, a keyboard, voice-recognition software that converts voice to text, or the like). In yet other embodiments, the message may include audio, video and/or text files and/or one or more network links (such as a hyperlink) that the network user enters by attaching and sending such file(s) and/or link(s) to the server 20, in a communication session with the server 20. In yet other embodiments, the message submitted by the network user is a combination of one or more of the above-described messages.

For example, a grandparent may submit a personal message (including an audio voice message, a video message, an image message and/or a text message) to the server 20 and designate the message as being for a comfort device 10 that is registered with a grandchild of that grandparent. The grandchild's comfort device 10 (such as a stuffed animal) receives the message when the comfort device 10 is located in the vicinity of the communication device 32 (such as, in the grandchild's house or room). Upon receipt of the message, the first display on the comfort device (such as a light on a heart-shaped feature of the stuffed animal) is activated to inform the grandchild that a message has been received. The grandchild may, then, activate the operator 28 (such as, by hugging the stuffed animal to activate a pressure-activated switch), to cause the electronic circuit 12 to play the message through the second display device 16 (such as a speaker and video screen on the stuffed animal). In other examples, personal messages may be submitted to friends, other family members, social or business acquaintances, or the like, in a similar manner.

While embodiments described above refer, primarily, to messages that are input to the server 20 by network users, via the network user's computer $NC^1, NC^2 \ldots NC^n$ or other processes. However, in further embodiments, messages may be obtained by server 20 from other sources. For example, in such embodiments, the server 20 has access to pre-stored messages (for example, stored in memory 34) that were provided by other sources and/or by the entity associated with running or managing the server 20 or website discussed above. Such pre-stored messages may include, for example, general greetings (such as, but not limited, greetings typically included in pre-printed greeting cards), or other pre-stored messages relating to specific topics. In such embodiments, the message input page (FIG. 5) includes a menu or field (not shown) for allowing the network user to select one or more pre-stored messages, as part of the network user's input.

In further embodiments, pre-stored messages were obtained by the server 20 from one or more other network sites, over the network 30, and stored in the memory 34. In yet further embodiments, links (network addresses or the like) for pre-stored messages are obtained by the server 20 and stored in the memory 34, for selection by a network user in a manner similar to the processes described above.

In further embodiments, the electronics 12 associated with a comfort device 10 includes a connector such as, but not limited to a USB connector, a cradle connector, or the like, for establishing a wired connection with a network-connected computer. The wired connection provides one or more of data and control signal connection, a power source connection, or the like. In such embodiments, a comfort device 10 may be connected to the server 20, through that connector connected to a network-connected computer associated with the device user. When so connected, the comfort device 10 can receive data and/or control information from the server 20, for controlling settings, message orders and other features. Alternatively or in addition, the comfort device 10 can receive power signals for charging a battery or other power supply (not shown) associated with the electronic circuit 12.

In the example shown in FIGS. 1 and 3, a comfort device 10 in the form of a stuffed bear is shown. However, as described above, embodiments of the present invention may be employed with other forms of comfort devices, such as, but not limited to, other stuffed animals, pillows, or other stuffed, plush or soft items typically handled and used in various manners for comfort (including cuddled, displayed, incorporated in games and other play activities, and the like).

Furthermore, while embodiments discussed above include first and second display devices 14 and 16, in further embodiments, the first display device 14 may be omitted, and the device user may play a message by activating the operator 18 at any desired time (i.e., without prompting by the activation of a first display device 14, as described above). For example, an embodiment of a comfort device 10 may be in the form of a pillow or other stuffed, plush or soft item that does not include a feature (such as the heart-shaped feature 18 described above) on which a first display device 14 is located. For such an embodiment, a device user may access a message that has been received and stored by the electronics 12, by squeezing the comfort device (or performing some other predefined manual operation on the comfort device) to activate the operator 18.

It is understood that the specific order or hierarchy of steps in the processes disclosed is an example of exemplary approaches. Based upon design preferences, it is understood that the specific order or hierarchy of steps in the processes may be rearranged while remaining within the scope of the present disclosure.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. In addition, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk, and Blu-Ray disc where disks usually reproduce data magnetically, while discs reproduce data optically with lasers. Combinations of the above should also be included within the scope of computer-readable media.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The invention claimed is:

1. A message playing system comprising:
a comfort device having a soft body and configured to be held or hugged to provide comfort to a device user;

an electronic circuit disposed within the body of the comfort device, the electronic circuit including a wireless communication circuit for receiving wireless electronic message communications;

a display device connected to the electronic circuit for displaying one or more messages associated with wireless electronic message communications received by the wireless communication circuit; and a further display device connected to the electronic circuit and controlled by the electronic circuit to display an indication that a message is available to be played, wherein the further display device that displays an indication that a message is available to be played is separate from the display device that displays the one or more messages received.

2. A system as recited in claim 1, wherein the wireless communication circuit comprises a WiFi communication circuit that communicates electronic messages through a direct wireless link to a wireless communication network.

3. A system as recited in claim 1, wherein the wireless communication circuit comprises a WiFi communication circuit that communicates electronic messages through a wireless link to a communication network, the wireless link including a network communication device connected via a wired connection to the communication network, the network communication device being connected for wireless communication with the wireless communication circuit in the comfort device.

4. A system as recited in claim 1, wherein the wireless communication circuit comprises a WiFi communication circuit that continuously or periodically monitors a wireless communication link for a wireless communication message.

5. A system as recited in claim 1, wherein the wireless communication circuit comprises at least one of a radio frequency (RF) or a Bluetooth communication circuit that communicates electronic messages through a direct wireless link to a wireless communication network.

6. A system as recited in claim 1, further comprising a server connected for communication with the comfort device, over a communication network, including at least one wireless communication link, the server configured to:
    receive over the communication network and store at least one message and identification information associated with the message, the identification information identifying the comfort device as being associated with the message; and
    transmit the at least one message from the server to the comfort device associated with the message.

7. A system as recited in claim 6, wherein the server is configured to transmit the at least one message to the comfort device in response to at least one of an expiration of a predetermined time period, a predefined time being reached, and a request being received from a user of the comfort device.

8. A system as recited in claim 6, further comprising an electronic memory disposed in the comfort device, the electronic memory for storing at least one message received from the server, wherein the server includes a further electronic memory for storing a plurality of messages and identification information associated with each message, and where the electronic memory disposed in the comfort device stores at least one message received from the server while the server stores at least one additional message and identification information that associates the at least one additional message with the comfort device.

9. A system as recited in claim 8, wherein the server is configured to transmit the at least one additional message to the comfort device in response to at least one of an expiration of a predetermined time period, a predefined time being reached, and a request being received from a user of the comfort device.

10. A system as recited in claim 1, further comprising a pressure activated electrical switch disposed in or on the comfort device and arranged to be activated upon the soft body of the comfort device being hugged.

11. A system as recited in claim 1, further comprising a housing containing the electronic circuit, the housing being sealed to inhibit leakage of fluid from outside of the housing to the electronic circuit contained within the housing, and a volume of stuffing around the housing.

12. A system as recited in claim 1, wherein the comfort device comprises a stuffed animal.

13. A system as recited in claim 1, further comprising:
    an electronic memory for storing one or more electronic messages received over a communication network from a remote server;
    wherein the electronic circuit is configured to activate the further display device upon a new electronic message being received and stored by the electronic memory, to inform a user that the new electronic message is available to be played.

14. A system as recited in claim 1, further comprising a server connected for communication with the comfort device, over a communication network, including at least one wireless communication link, the server providing a network site at which one or more network users are able to enter message information and designate a comfort device to associate with the message information, the server configured to communicate message information to the comfort device designated as being associated with the message information.

15. A system as recited in claim 1, further comprising an electrical switch and detection circuit disposed in or on the comfort device for activating the display device to display one or more messages, the electrical switch and detection circuit configured to activate the display device upon detection of at least one of light and motion in the proximity of the comfort device.

16. A message playing system comprising:
    a plurality of comfort devices, each comfort device having a soft body and configured to be held or hugged to provide comfort to a device user, each comfort device including an electronic circuit disposed within the body of the comfort device, the electronic circuit including a wireless communication circuit for receiving wireless electronic message communications, each comfort device including a display device connected to the electronic circuit for displaying one or more messages associated with wireless electronic message communications received by the wireless communication circuit; and
    a server connected for communication with the plurality of comfort devices, over a communication network, including at least one wireless communication link to each comfort device, the server configured to receive over the communication network and store a plurality of messages and identification information for each message, the identification information for each message identifying at least one of the comfort devices as being associated with the message, the server further configured to transmit the plurality of messages from the server to the comfort devices associated with the messages.

17. A message playing system that operates with plurality of comfort devices, where each comfort device has a soft body and configured to be held or hugged to provide comfort to a device user, an electronic circuit disposed within the soft body for receiving wireless electronic message communications, and a display device for displaying one or more messages associated with one or more received wireless electronic message communications, the system comprising:

a server connected for communication with the plurality of comfort devices, over a communication network, including at least one wireless communication link to each comfort device, the server configured to:

receive over the communication network and store a plurality of messages and identification information for each message, the identification information for each message identifying at least one of the comfort devices as being associated with the message; and transmit the plurality of messages from the server to the comfort devices associated with the messages, including transmitting at least one message to at least one comfort device identified by the identifying information for that at least one message without transmitting that at least one message to at least one other comfort device that is not identified by the identifying information for that at least one message.

18. A system as recited in claim 17, wherein the server is configured to transmit the at least one message to the comfort device in response to at least one of an expiration of a predetermined time period, a predefined time being reached, and a request being received from a user of the comfort device.

19. A system as recited in claim 17, wherein transmitting at least one message to at least one comfort device comprises transmitting a plurality of messages for playing in a sequence on the at least one comfort device, wherein the server is configured to receive over the communication network additional information corresponding to the sequence in which the plurality of messages are to be delivered to or played by the comfort device.

* * * * *